(12) United States Patent
Li

(10) Patent No.: US 9,358,532 B2
(45) Date of Patent: Jun. 7, 2016

(54) CATALYST FOR ASYMMETRIC HYDROGENATION OF IMINE, SYNTHESIS METHOD AND APPLICATION THEREOF

(75) Inventor: Jin Li, Liaoning (CN)

(73) Assignees: Dalian Heterogeneous Catalyst Co. Ltd., Liaoning (CN); Jiangsu Yangnong Chemical Co., Ltd., Jiangsu (CN); Youth Chemical Co., Ltd., Jiangsu (CN)

( * ) Notice: Subject to any disclaimer, the term of this patent is extended or adjusted under 35 U.S.C. 154(b) by 0 days.

(21) Appl. No.: 14/001,756

(22) PCT Filed: Mar. 2, 2011

(86) PCT No.: PCT/CN2011/071448
§ 371 (c)(1),
(2), (4) Date: Sep. 19, 2013

(87) PCT Pub. No.: WO2012/116493
PCT Pub. Date: Sep. 7, 2012

(65) Prior Publication Data
US 2014/0018548 A1 Jan. 16, 2014

(30) Foreign Application Priority Data
Feb. 28, 2011 (CN) .......................... 2011 1 0048240

(51) Int. Cl.
*B01J 31/24* (2006.01)
*C07C 231/10* (2006.01)
*B01J 31/18* (2006.01)
*C07C 231/02* (2006.01)
*C07C 251/08* (2006.01)
*C07F 9/6571* (2006.01)
*C07C 213/02* (2006.01)
*C07D 333/36* (2006.01)

(52) U.S. Cl.
CPC ............ *B01J 31/2466* (2013.01); *B01J 31/186* (2013.01); *C07C 213/02* (2013.01); *C07C 231/02* (2013.01); *C07C 231/10* (2013.01); *C07C 251/08* (2013.01); *C07D 333/36* (2013.01); *C07F 9/657154* (2013.01); *B01J 2231/643* (2013.01); *B01J 2531/007* (2013.01); *B01J 2531/0266* (2013.01); *B01J 2531/827* (2013.01); *C07B 2200/07* (2013.01)

(58) Field of Classification Search
CPC ............ C07B 2200/07; B01J 2531/007; B01J 31/2466; B01J 2531/827; B01J 31/186; B01J 2231/643; B01J 2531/0266; C07C 231/02; C07C 251/08; C07C 231/10; C07C 233/25; C07C 213/02; C07C 217/08; C07D 333/36; C07F 9/657154
USPC ........ 549/68; 564/214, 276; 502/167; 568/12
See application file for complete search history.

(56) References Cited

U.S. PATENT DOCUMENTS

| 4,994,615 A | 2/1991 | Spindler et al. ............... 564/304 |
| 5,011,995 A | 4/1991 | Pugin et al. ..................... 64/302 |
| 5,112,999 A | 5/1992 | Osborn et al. ................... 556/23 |
| 5,466,844 A | 11/1995 | Spindler et al. ................. 556/11 |

(Continued)

FOREIGN PATENT DOCUMENTS

| CN | 1951945 A | 4/2007 |
| CN | 101857612 A | 10/2010 |
| WO | WO 97/02232 A1 | 1/1997 |

OTHER PUBLICATIONS

CN 1951945 A; GPSN Chinese-English Machine Translation—annotated—Apr. 9, 2014, p. 1-15.*
Mrsic, A., Asymmetric Hydrogenation of Imines, Enamines and N Heterocycles Using Phosphoramidite Ligands, 2010, University of Groningen, p. 1-236, accessed Apr. 10, 2014; http://irs.ub.rug.nl/ppn/32413780X.*

(Continued)

*Primary Examiner* — Samantha Shterengarts
*Assistant Examiner* — Matt Mauro
(74) *Attorney, Agent, or Firm* — Fitzpatrick, Cella, Harper & Scinto

(57) ABSTRACT

A chiral hydrogenated $H_8$-BINOL bisphosphine compound is provided, with the structure shown as the following formula (I), wherein both $R^1$ and $R^2$ are halogen, H or $C_1$-$C_{10}$ aliphatic group; $R^3$ is H or $C_1$-$C_{10}$ aliphatic group; $R^4$ is halogen, amino, nitro, H, $C_1$-$C_{10}$ aliphatic group or $C_1$-$C_{10}$ aromatic group; and X is phenyl, substituted phenyl, cyclohexyl, substituted cyclohexyl, $C_6$-$C_{30}$ aromatic group, or $C_6$-$C_{30}$ heterocyclic aromatic group containing one or more heteroatoms selected from N, S, O. The present invention further provides a catalyst for an asymmetric catalytic hydrogenation reaction which contains the compound, wherein the catalyst can produce more than 90% of enantiomers and efficiency with the turnover number of greater than 100,000 in the asymmetric hydrogenation reaction of imines.

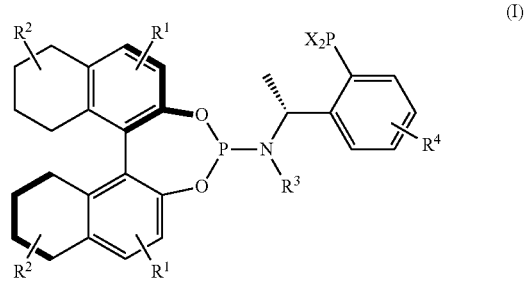

16 Claims, No Drawings

(56) References Cited

U.S. PATENT DOCUMENTS

| | | | |
|---|---|---|---|
| 5,563,308 A | 10/1996 | Spindler et al. | 585/277 |
| 5,859,300 A | 1/1999 | Jalett et al. | 564/143 |
| 5,886,225 A | 3/1999 | Jalett et al. | 564/415 |
| 6,008,393 A | 12/1999 | Sablong et al. | 556/18 |
| 6,527,293 B1 | 3/2003 | Roy et al. | 280/624 |

OTHER PUBLICATIONS

Eggenstein, M.,"Highly Efficient and Versatile Phosphine-Phosphoramidite Ligands for Asymmetric Hydrogenation." Advanced Synthesis & Catalysis 351.5 (2009): 725-732.*

M. Eggenstein et al., "Highly Efficient and Versatile Phosphine-Phosphoramidite Ligands for Asymmetric Hydrogenation," *Advanced Synthesis & Catalysis*, vol. 351, No. 5, pp. 725-732 (2009).

X.-M. Zhou et al., "Chiral 1-phenylethylamine-derived phosphine-phosphoramidite ligands for highly enantioselective Rh-catalyzed hydrogenation of β-(acylamino)acrylates: significant effect of substituents on 3,3'-positions of binaphthyl moiety," *Organic & Biomolecular Chemistry*, vol. 8, No. 10, pp. 2320-2322 (2010).

H.-U. Blaser et al., "The Chiral Switch of Metolachlor: The Development of a Large-Scale Enantioselective Catalytic Process," *Chimia*, vol. 53, No. 5, pp. 275-280 (1999).

\* cited by examiner

CATALYST FOR ASYMMETRIC HYDROGENATION OF IMINE, SYNTHESIS METHOD AND APPLICATION THEREOF

FIELD OF THE INVENTION

The present invention belongs to the asymmetric catalysis field of chiral pesticides or pharmaceuticals, and in particular relates to a catalyst for an asymmetric hydrogenation reaction and a preparation method and use thereof.

BACKGROUND OF THE INVENTION

In an asymmetric synthesis reaction, asymmetric catalysis is one of the most effective and most economically valuable methods for obtaining chiral compounds. A large amount of a new optically active substance can be obtained from a small amount of a chiral catalyst by asymmetric catalysis, thus not only avoiding the cumbersome resolution of a raceme obtained by a general synthetic method, but also avoiding requiring a large amount of a chiral reagent like stoichiometric asymmetric synthesis. Asymmetric hydrogenation of imines is a core technology in asymmetric synthesis and one of the most effective methods for synthesizing optically pure chiral drugs, pesticides, food additives and flavorings while the design and synthesis of chiral ligands are key factors to realize this core technology. The currently most effective chiral catalyst for an asymmetric hydrogenation reaction of imines is mainly an iridium and rhodium catalyst system, and chiral ligands include diphosphine ligands and nitrogen-phosphine ligands. However, most of these chiral ligands either are difficult to synthesize or have low catalytic activity and stereoselectivity, so it is difficult to have industrial application. The currently most successful catalyst system is a catalyst system formed by a JosiPhos ferrocenyldiphosphine ligand and an iridium metal compound, and has been successfully applied to the industrial production of a chiral herbicide metolachlor with an annual output of more than 10,000 tons. U.S. Pat. No. 622,118, U.S. Pat. No. 5,886,225, U.S. Pat. No. 6,008,393, U.S. Pat. No. 5,859,300, WO9702232, U.S. Pat. No. 6,527,293, U.S. Pat. No. 5,563,308 and U.S. Pat. No. 5,466,844 describe a process for the hydrogenation of imines, wherein in the presence of an iridium catalyst synthesized by a chiral diphosphine ligand with ferrocene as a matrix, the reaction mixture is added with a halide and contains an acid, which can improve the catalyst activity by tens of times or higher and meanwhile can reduce or avoid catalyst deactivation. When the temperature is higher than 50° C., the reaction optical yield of 88% can be achieved only. U.S. Pat. No. 4,994,615 describes a process for the asymmetric hydrogenation of prochiral N-arylketimines, wherein iridium catalysts having chiral diphosphine ligands are used. U.S. Pat. No. 5,011,995 describes a process for the asymmetric hydrogenation of prochiral N-arylketimines using the same catalysts. U.S. Pat. No. 5,112,999 discloses polynuclear iridium compounds and a complex salt of iridium, which contain diphosphine ligands, as catalysts for the hydrogenation of imines. In the case of relatively large batches or on an industrial scale, the catalysts tend to become deactivated to different extents depending on the catalyst precursor, the substrate and the diphosphine ligands that are used. Also at elevated temperatures, the reaction substrate cannot be completely converted. The Chinese Patent CN101857612 reports a class of chiral diphosphine ligands and iridium-complexed catalysts, wherein the catalysts have a certain hydrogenation activity on imines with a carbon-nitrogen double bond, but are difficult for industrial application due to the turnover number of the hydrogenation for the carbon-nitrogen double bond (imines) up to 10,000. Accordingly, in industrial application, the hydrogenation processes provide too low catalyst yield in terms of economic feasibility, so the current study focuses on the development of a novel and efficient catalyst system.

SUMMARY OF THE INVENTION

An object of the present invention is to provide a novel chiral hydrogenated bisphosphine compound.

Another object of the present invention is to provide a catalyst for an asymmetric catalytic hydrogenation reaction, which comprises a coordination compound with the compound mentioned above as a ligand and has higher hydrogenation activity.

The above objects of the present invention are realized by the following technical solution:

A chiral hydrogenated $H_8$-BINOL bisphosphine compound is provided, with the structure shown as the following formula (I):

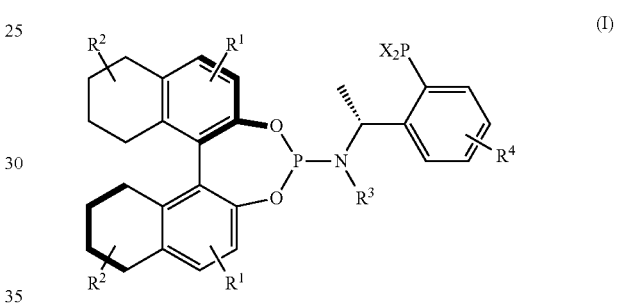

wherein both $R^1$ and $R^2$ are halogen, H or $C_1$-$C_{10}$ aliphatic group; $R^3$ is H or $C_1$-$C_{10}$ aliphatic group; $R^4$ is halogen, amino, nitro, H, $C_1$-$C_{10}$ aliphatic group or $C_1$-$C_{10}$ aromatic group; and X is phenyl, substituted phenyl, cyclohexyl, substituted cyclohexyl, $C_6$-$C_{30}$ aromatic group, or $C_6$-$C_{30}$ heterocyclic aromatic group containing one or more heteroatoms selected from N, S, O.

Preferably, in the chiral hydrogenated $H_8$-BINOL bisphosphine compound, X may be selected from any one of the following structures:

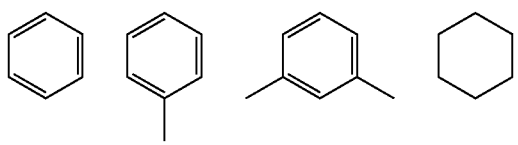

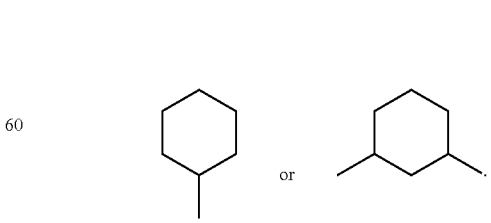

A synthetic route and method of the chiral hydrogenated $H_8$-BINOL bisphosphine compound is as follows:

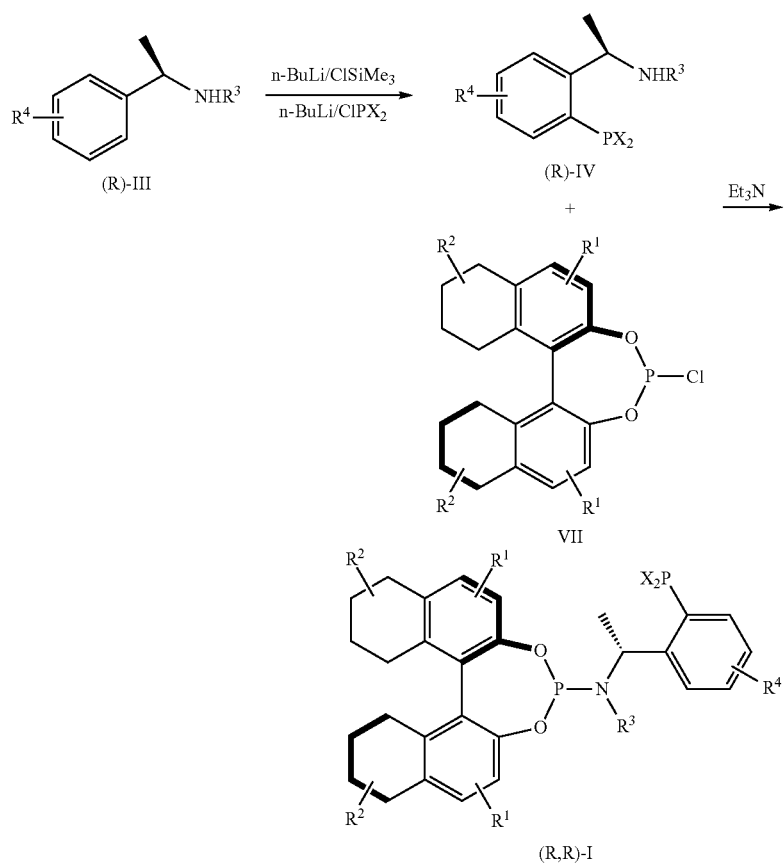

It can be seen from the above synthetic route that the chiral hydrogenated H$_8$-BINOL bisphosphine compound is synthesized by a multi-step reaction starting from chiral derived (R)-phenylethylamine (III). The method comprises: first directly lithiating and phosphorylating the ortho position of a primary amine to synthesize derived 1-(2-disubstituted-phosphine)phenylethylamine (IV); and then condensating the derived 1-(2-disubstituted-phosphine)phenylethylamine (IV) with chiral phosphine-containing hydrogenated chloro-H$_8$-BINOL(R-IV) to obtain the chiral hydrogenated H$_8$-BINOL bisphosphine compound I with different chiral centers according to the present invention. The synthetic steps comprise:

(1) based on molar ratio of chiral derived (R)-phenylethylamine (III):n-BuLi (n-butyllithium):ClSiMe$_3$ (trimethylchlorosilane):n-BuLi:ClPX$_2$ (di-substituted-chlorophosphine)=1:1-3:1-3:3-6:1-5, dissolving chiral derived (R)-phenylethylamine (III) in ethyl ether; continuously adding n-BuLi and ClSiMe$_3$ at 0° C.; adding n-BuLi to the reaction mixture after 0.5-10 h; keeping reaction for 2-10 h; adding the resulting reaction mixture to a solution of ClPX$_2$ under cooling condition; the reaction is left standing overnight at 0-50° C.; adding 2M HCl (hydrochloric acid) to quench the reaction; and performing column chromatography to obtain a phosphine-amine compound (R)-IV; wherein, in the compound (III), R$^3$ is H or C$_1$-C$_{10}$ aliphatic group; and R$^4$ is halogen, amino, nitro, H, C$_1$-C$_{10}$ aliphatic group or C$_1$-C$_{10}$ aromatic group; and in the compound ClPX$_2$, X is phenyl, substituted phenyl, cyclohexyl, substituted cyclohexyl, C$_6$-C$_{30}$ aromatic group, or C$_6$-C$_{30}$ heterocyclic aromatic groups containing one or more heteroatoms selected from N, S, O;

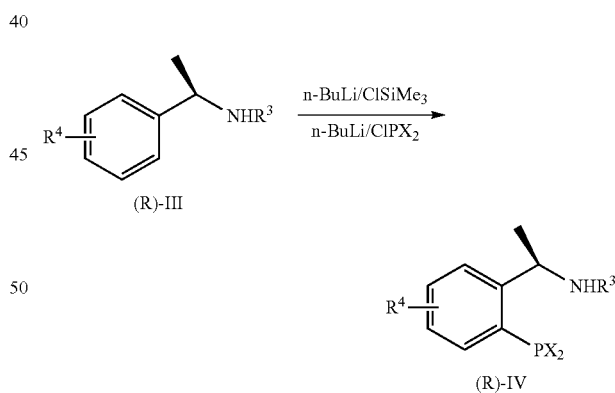

(2) based on weight ratio of derived BINOL(R-V): rhodium/platinum on carbon:ethanol=1:0.01-0.2:1-10, adding BINOL(V), a hydrogenation catalyst rhodium/platinum on carbon and ethanol to an autoclave; replacing with hydrogen for several times; then warming up to 10-100° C.; increasing hydrogen pressure to 5-40 atm; and after hydrogen is no longer absorbed in the reaction, cooling, filtering and removing the solvent under vacuum, thereby obtaining derived hydrogenated H$_8$-BINOL(VI); wherein, in the compound V, both R$^1$ and R$^2$ are halogen, H or C$_1$-C$_{10}$ aliphatic group;

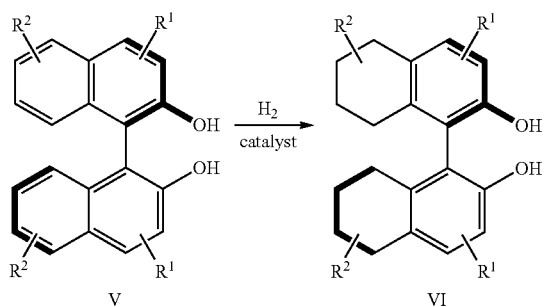

(3) based on molar ratio of the compound VI obtained in step (2): PCl₃ (phosphorus trichloride): NMP (2-methylpyrrolidone)=1:5-10:0.001-0.01, charging compound VI obtained in step (2) and phosphorus trichloride into a reaction flask; adding a catalytic amount of 2-methylpyrrolidone; heating under reflux to react until chiral hydrogenated $H_8$-BINOL is fully dissolved; remove the solvent under vacuum; and recrystallizing the residue with n-hexane to obtain phosphine-containing hydrogenated chloro-$H_8$-BINOL(VII);

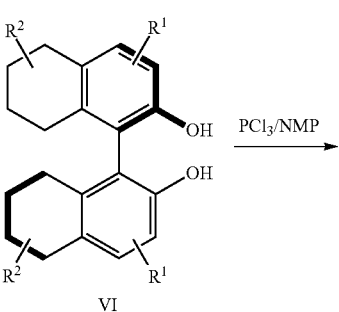

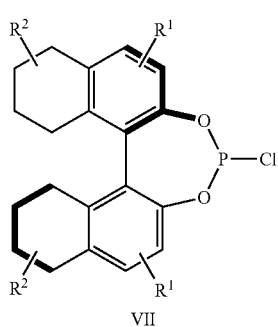

and (4) based on molar ratio of compound IV obtained in step (1):the compound VII obtained in step (2):Et₃N(triethylamine)=1:1-2:3-5, dissolving compound VII in toluene; adding a solution of compound (R)-IV and NEt₃ in toluene at 0-50° C.; warming up the reaction mixture to 0-95° C.; reacting for 1-30 h under stirring; filtering and removing the solvent, thereby obtaining the chiral hydrogenated $H_8$-BINOL diphosphine ligand I according to the present invention;

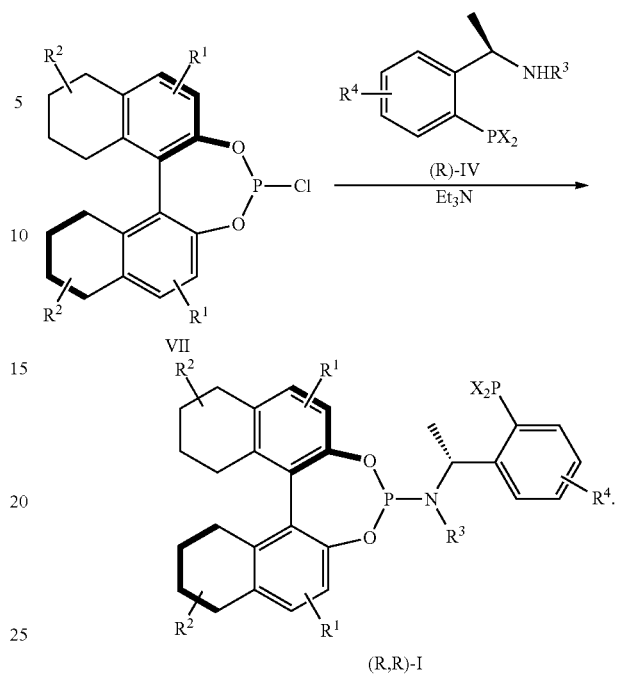

The present invention further provides a catalyst for an asymmetric catalytic hydrogenation reaction, which comprises a coordination compound formed by the chiral hydrogenated $H_8$-BINOL bisphosphine compound as a ligand and an iridium-cyclooctadiene complex based on a molar ratio of 0.5-5:1.

The iridium (Ir)-cyclooctadiene complex is a coordination compound formed by reacting an inorganic or organic compound of iridium with cyclooctadiene and is selected from any one of [IrCl(COD)]₂, [IrBr(COD)]₂ or [Ir(COD)₂]BF₄.

All of the coordination compounds [IrCl(COD)]₂, [IrBr (COD)]₂ and [Ir(COD)₂]BF₄ are compounds known in the art and can be prepared with reference to a method in relevant literature (Blaser h u, et al, Chimia 1999, 53, 275).

The catalyst for an asymmetric catalytic hydrogenation reaction preferably further comprises a halogen-containing additive, a molar ratio of which to the iridium-containing coordination compound catalyst is 0.001-10:1.

The halogen-containing additive is preferably an alkali metal salt of a halogen family element, a halogen-containing C1-C60 quaternary ammonium salt, or a halogen-containing C1-C60 aromatic hydrocarbon or aliphatic hydrocarbon.

The halogen is preferably chlorine, bromine or iodine.

The halogen-containing additive is further preferably iodobenzene, tetrabutyl ammonium iodide or other iodine-containing C1-C60 quaternary ammonium salt.

The present invention further provides use of said catalyst in the following asymmetric catalytic hydrogenation reactions:

(1) catalytic asymmetric hydrogenation of N-alkyl, N-arylimine or N-aromatic heterocyclic imine;
(2) catalytic asymmetric hydrogenation of N-acyl hydrazone, sulfimide or phosphinoimide; or
(3) catalytic asymmetric hydrogenation of an aromatic or non-aromatic azacyclic ring.

The asymmetric catalytic hydrogenation reaction is carried out at a temperature of −20 to 150° C.

The asymmetric catalytic hydrogenation reaction is carried out at a pressure of 5-150 atm.

The molar ratio of a reaction substrate and the catalyst is preferably 50-500,000:1 in the asymmetric hydrogenation reaction.

An organic or inorganic acid additive is used in the asymmetric hydrogenation reaction which is added in an amount of 0.001-60% based on the weight of the substrate.

The organic or inorganic acid additive is preferably one of acetic acid, chloroacetic acid, propionic acid, trifluoroacetic acid, sulfuric acid, phosphoric acid or methanesulfonic acid, or a mixture of more than two thereof.

In the asymmetric hydrogenation reaction, the N-arylimine or N-aromatic heterocyclic imine preferably has the following structures:

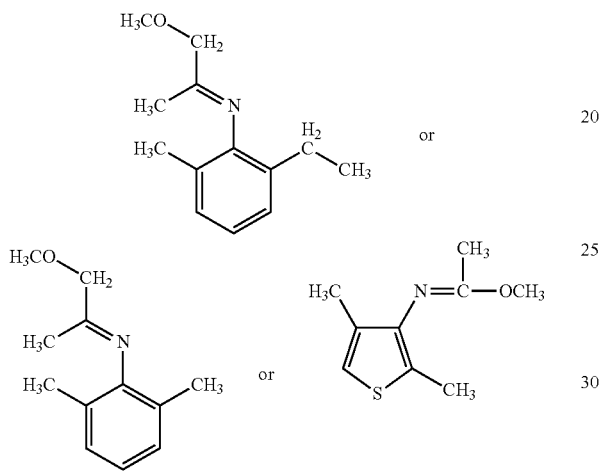

The present invention further provides use of said catalyst in the preparation of a chiral herbicide (S)-metolachlor, wherein the N-arylimine, preferably N-(2'-methyl-6'-ethylphenyl)-N-(1-methoxylmethyl)ethylimine is catalyzed with the catalyst to obtain a chiral hydrogenated product (S)—N-(2'-methyl-6'-ethylphenyl)-N-(1-methoxylmethyl) ethylamine ((S)-NAA), and then the chiral hydrogenated product is used as a precursor to synthesize the chiral herbicide (S)-metolachlor.

A method for synthesizing the chiral herbicide (S)-metolachlor comprises is as follows:

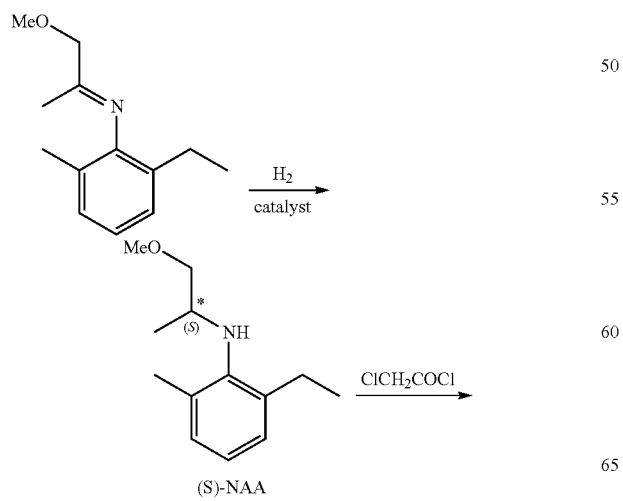

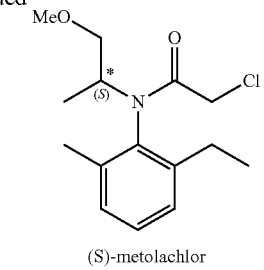

(1) based on molar ratio of EMA-imine: (R,R)-I:[IrCl(COD)]$_2$:an additive:a solvent=1:0.000001-0.0000005: 0.000001-0.000005:0.1-0.0001:1-10, adding EMA-imine, the additive and the solvent to a circulation hydrogenation reactor; replacing with high-purity hydrogen for several times; then pressing a catalyst solution of (R,R)-I into the reactor; and keeping a reaction temperature at −20 to 100° C., a reaction pressure at 5-150 atm and a reaction time of 1-30 h to obtain (S)-NAA, wherein the conversion rate is greater than 99% and the content of a chiral (S)-enantiomer is greater than 90%;

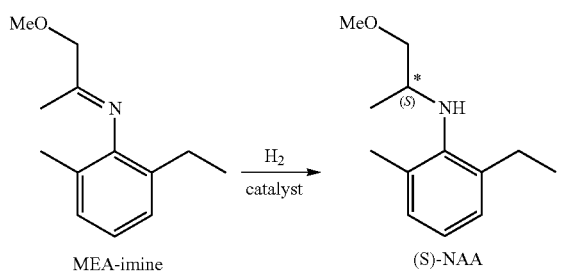

(2) in the presence of acid-binding agents such as pyridine and triethylamine, mixing (S)-NAA with chloroacetyl chloride to have an acylation reaction at −20 to 100° C., thereby generating (S)-metolachlor.

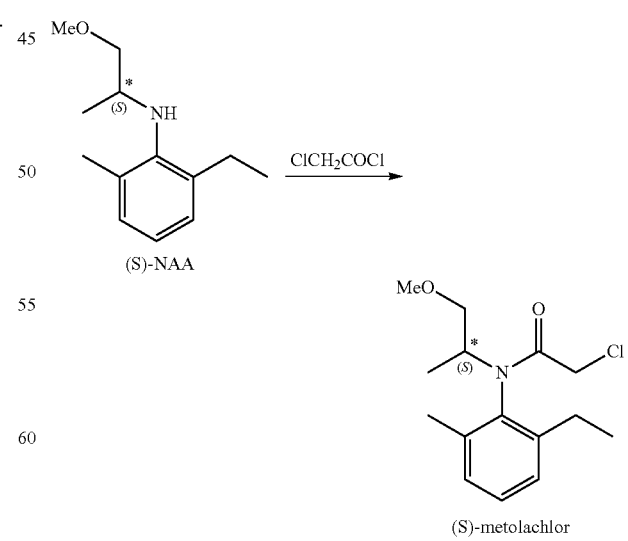

The high effective catalytic system according to the present invention consisting of a chiral hydrogenated H$_8$-BINOL diphosphine ligand and auxiliary agents including an iridium-containing coordination compound and a halogen-containing compound exhibits excellent characteristics in an asymmetric hydrogenation reaction of imines, wherein more than 90% of enantiomers can be obtained and the turnover number is greater than 100,000. The ligand has a novel structure and stable properties. Compared with the existing diphosphine ligand (R)—(S)-xyliphos applied in chiral industry, synthetic method for the ligand is simple and has a low price; and a catalyst formed by the ligand and iridium metal has high activity and stereoselectivity in a catalytic asymmetric hydrogenation reaction of an imine double bond.

The particular embodiments of the present invention are provided below and can illustrate a chiral ligand and a method for preparing a catalyst and its use in asymmetric hydrogenation of imines and synthesis of (S)-metolachlor that are involved in the present invention without limit the claims of the present invention.

EXAMPLES

Example 1

Preparation of Compound (R,R)-IA ($R_1$, $R_2$, $R_3$ and $R_4$ are H, and X is Phenyl in its General Structural Formula)

1) To a 300 ml three-neck flask were added 3.48 g (R)-1-phenylethylamine and 20 ml ethyl ether, and was slowly added 17.96 ml of a hexane solution of n-BuLi with a concentration of 3.2 mol/l at room temperature. After addition, the reaction was continuously stirred at 0° C. for 15 min and then 3.99 ml trimethylchlorosilane was added. 53.7 ml of a hexane solution of n-BuLi with a concentration of 1.6 mol/l was slowly added after 1-2 h of reaction time and the resulting reaction mixture was slowly warmed up to room temperature within 5 h. After 1 h of reaction time, the resulting reaction mixture was cooled to −20° C. and a solution of 5.16 ml diphenyl phosphine chloride and 20 ml ethyl ether was slowly added. The reaction was warmed up to room temperature and stirred overnight. 60 ml saturated aqueous $NaHCO_3$ was added and then the reaction was continuously stirred for 10 min. The liquid was separated, the aqueous layer was extracted twice with 75 ml ethyl ether, and ether layers were combined, washed with 200 ml water and dried with anhydrous $Na_2SO_4$. The resulting mixture was filtered, the solvent is removed with vacuum, the residue was subjected to column chromatography to obtain a viscous liquid which was recrystallized with n-hexane to give a white crystal, i.e., a phosphine-amine compound (R)-IV (7.4 g; yield: 75%). $[\alpha]_D^{13}=-56.7$ (c 0.53, $CHCl_3$); $^1H$ NMR ($CDCl_3$): δ1.23 (d, J=6.8 Hz, 3H), 1.38 (s, 2H), 4.90 (m, 1H), 6.83-7.59 (m, 14H); $^{31}P$ NMR ($CDCl_3$): δ-16.3; $^{13}C$ NMR δ24.3, 47.5, 124.8, 126.5, 128.1, 128.3, 129.0, 132.8, 133.2, 133.4, 136.1, 136.2, 136.5, 136.6, 151.3, 151.5. HRMS (m/z) calcd for $C_{20}H_{20}NP+H$: 306.1412. found: 306.1406.

2) To a 200 ml three-neck flask were added 20 g BINOL ((R)-V), 100 ml solvent ethanol and 0.2 g rhodium on carbon, hydrogen at 10 atm was introduced for hydrogenation, then the catalyst was filtered, and ethanol was evaporated to give 21 g chiral hydrogenated $H_8$-BINOL(R)-VI.

3) 21 g (R)-VI obtained in step 2), 150 g $PCl_3$ and a catalytic amount of 2-methylpyrrolidone were reacted under reflux until the solid disappeared (about 10 min). Majority of $PCl_3$ is removed under vacuum and a small amount of residual $PCl_3$ was removed by azeotropy with toluene under vacuum. After toluene was removed, the residue was recrystallized with n-hexane to give white chiral phosphine-containing hydrogenated chloro-$H_8$-BINOL (R)-VII (24 g).

4) To a 200 ml three-neck flask were added 7.2 g of (R)-VII obtained in step 3) and 60 ml anhydrous toluene, and a solution of 7.1 g of the compound (R)-IV obtained in step 1) and 6.06 g triethylamine in 20 ml toluene was slowly added dropwise at 0° C. After addition, the resulting reaction mixture was warmed up to room temperature and the reaction was continuously stirred overnight. The resulting mixture was filtered and washed with toluene. The residue was dissolved in $CH_2Cl_2$, washed with water and dried with anhydrous $Na_2SO_4$. The solvent was removed to give a white powdery chiral hydrogenated $H_8$-BINOL bisphosphine compound (9.52 g) which was recorded as compound (R,R)-IA. $^1HNMR$ (400 MHz, $CDCl_3$): δ1.41 (d, J=6.8 Hz, 3H), 1.53-1.56 (m, 2H), 1.75-1.81 (m, 6H), 2.23-2.27 (m, 2H), 2.63-2.82 (m, 2H), 3.31-3.34 (m, 4H), 5.38 (m, 1H), 6.87 (m, 18H); $^{31}P$ NMR ($CDCl_3$): δ-16.92, 145.33; $^{13}C$ NMR δ22.5, 22.7, 22.8, 23.0, 26.1, 27.7, 48.3, 118.5, 119.5, 125.8, 127.2, 128.5, 128.6, 128.8, 129.1, 129.5, 133.2, 133.7, 133.9, 134.0, 134.2, 137.7, 137.8, 145.0, 148.5, 150.6.

Example 2

Preparation of Compound (R,R)-IB ($R_1$, $R_2$ and $R_4$ are H, $R_3$ is —$CH_3$, and X is Phenyl in its General Structural Formula)

1) The phosphine-amine compound (R)-IV (1.22 g, 4 mmol) obtained in step 1) in Example 1 and ethyl formate (1.45 ml) were used and stirred to react overnight at temperature of 30-60° C., the solvent was removed by rotary evaporation, the resulting mixture was dried under vacuum to give a crude product as a solid foam, which is used in the next step without purification.

2) To a 100 ml three-neck flask were added $LiAlH_4$ (0.27 g) and THF (10 ml) under argon atmosphere, the above crude product was dissolved in 10 ml THF and then slowly added dropwise to the three-neck flask, and the reaction was vigorously exothermic. After dropwise addition, the resulting reaction mixture was refluxed for 5-10 h, then reflux was stopped, the reaction mixture was cooled to 0-10° C., and 10% aqueous KOH solution was carefully added dropwise to quench the reaction. The reaction mixture was suction-filtered by a sand-core funnel and the filter cake was washed with tetrahydrofuran. The filtrate was dried with anhydrous $Na_2SO_4$. The solvent is removed under vacuum, the residue was subjected to column chromatography (silica gel; petroleum ether/ethyl acetate/triethylamine: 10/1/1) to remove the solvent, and was recrystallized with n-hexane to give a methylated phosphine-amine compound (R)-IVB as a white solid (yield: 52%); $^1HNMR$ (400 MHz, $CDCl_3$): $[\alpha]_D^{23}=-57.1$ (c 0.48, $CHCl_3$); $^1NMR$ ($CDCl_3$): δ1.19-1.22 (d, J=12 Hz, 3H), 2.14 (s, 3H), 4.46-4.51 (m, 1H), 6.84-7.53 (m, 14H); $^{31}P$ NMR ($CDCl_3$): δ-16.5; $^{13}C$ NMR δ23.2, 34.2, 56.6, 125.8, 125.9, 126.9, 128.5, 128.6, 128.7, 129.4, 133.4, 133.8, 134.0, 134.2, 135.2, 136.7, 136.8, 137.0, 137.1, 149.8, 150.0; HRMS (m/z) calcd for $C_{21}H_{22}NP$: 319.1490. found: 319.1492.

3) To a 200 ml three-neck flask were added 20 g BINOL ((R)-V), 100 ml solvent ethanol and 0.2 g rhodium on carbon, hydrogen at 10 atm was introduced for hydrogenation, then the catalyst was filtered, and ethanol was evaporated to give 21 g chiral hydrogenated (R)$H_8$-BINOL ((R)-VI).

4) (R)-VI obtained in step 3), 150 g $PCl_3$ and a catalytic amount of 2-methylpyrrolidone were reacted under reflux until the solid disappeared (about 10 min). Majority of $PCl_3$ is removed under vacuum and a small amount of residual $PCl_3$ was removed by azeotropy with toluene under vacuum. After toluene was removed, the residue was recrystallized with n-hexane to give white chiral phosphine-containing hydrogenated chloro-$H_8$-BINOL ((R)-VII: 24 g).

5) To a 200 ml three-neck flask were added 7.2 g of (R)-VII obtained in step 4) and 60 ml anhydrous toluene, and a solution of 7.1 g of the compound (R)-IVB obtained in step 2) and 6.06 g triethylamine in 20 ml toluene was slowly added dropwise at 0° C. After addition, the resulting reaction mixture was warmed up to room temperature and the reaction was continuously stirred overnight. The resulting mixture was filtered and washed with toluene. The residue was dissolved in $CH_2Cl_2$, washed with water and dried with anhydrous $Na_2SO_4$. The solvent was removed to give a white powdery methylated hydrogenated $H_8$-BINOL bisphosphine compound (10.2 g) which was recorded as compound (R,R)-IB. $^1$HNMR (400 MHz, $CDCl_3$): δ1.52-1.60 (m, 5H), 1.73-1.78 (m, 6H), 1.85 (m, 2H), 2.16-2.24 (m, 2H), 2.73-2.80 (m, 6H), 5.30 (m, 1H), 6.77-7.73 (m, 18H); $^{31}$P NMR ($CDCl_3$): δ-17.7, 141.0; $^{13}$C NMR δ21.9, 22.5, 22.7, 27.6, 29.1, 30.3, 56.9, 118.4, 118.8, 126.7, 128.1, 128.4, 128.5, 129.0, 132.6, 133.8, 134.0, 134.2, 137.2, 137.8, 148.9.

Example 3

Preparation of Compound (R,R)-IC with the Following Structure ($R_1$, $R_2$, $R_3$ and $R_4$ are H, and X is Cyclohexyl in its General Structural Formula)

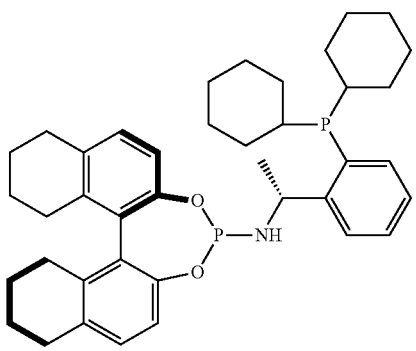

1) To a 200 ml three-neck flask were added 2.78 g (R)-1-phenylethylamine and 25 ml ethyl ether, and was slowly added 14.35 ml of a hexane solution of n-BuLi with a concentration of 3.2 mol/l at room temperature. After addition, the reaction was continuously stirred at 0° C. for 15 min and then 3.19 ml trimethylchlorosilane was added. 42.9 ml of a hexane solution of n-BuLi with a concentration of 1.6 mol/l was slowly added after 1-2 h of reaction time and the resulting reaction mixture was slowly warmed up to room temperature within 5 h. After 1 h of reaction time, the resulting reaction mixture was cooled to −20° C. and a solution of 5.6 ml dicyclohexylchlorophosphine and 20 ml ethyl ether was slowly added. The reaction was warmed up to room temperature and stirred overnight. 48 ml saturated aqueous $NaHCO_3$ was added and then the reaction was continuously stirred for 10-30 min. The liquid was separated, the aqueous layer was extracted twice with 60 ml ethyl ether, and ether layers were combined, washed with 100 ml water and dried with anhydrous $Na_2SO_4$. The resulting mixture was filtered, the solvent is removed with vacuum, the residue was subjected to column chromatography to obtain a viscous liquid which was recrystallized with n-hexane to give a white crystal, i.e. a phosphine-amine compound (R)-IV (yield: 58%). $^1$HNMR (400 MHz, $CDCl_3$): δ1.49 (d, J=8.0 Hz, 3H); 2.15 (s, 3H); 2.30 (s, 6H); 5.20 (m, 1H), 6.91-7.60 (m, 22H); $^{31}$P NMR ($CDCl_3$): δ-17.25, 48.58; $^{13}$C NMR δ22.3; 22.7; 59.9; 126.8; 126.9; 128.4; 128.5; 128.6; 128.8; 129.1; 131.8; 132.0; 132.7; 132.9; 133.8; 134.0; 137.6; 150.2; 150.5.

2) To a 200 ml three-neck flask were added 6.5 g of chiral phosphine-containing hydrogenated chloro-$H_8$-BINOL(R)-VII (prepared according to step 4) in Example 1) and 60 ml anhydrous toluene, and a solution of 5.3 g of the compound (R)-IV obtained in step 1) and 5.45 g triethylamine in 18 ml toluene was slowly added dropwise at 0° C. After addition, the resulting reaction mixture was warmed up to room temperature and the reaction was continuously stirred overnight. The resulting mixture was filtered and washed with toluene. The residue was dissolved in $CH_2Cl_2$, washed with water and dried with anhydrous $Na_2SO_4$. The solvent was removed to give a white powdery chiral hydrogenated $H_8$-BINOL diphosphine ligand (7.31 g) which was recorded as compound (R,R)-IC. 1HNMR (400 MHz, CDCl3): 1.24-2.27 (m, 25H), 2.28-2.33 (m, 2H), 2.64-2.80 (m, 2H), 3.27-3.31 (m, 4H), 5.36-5.38 (m, 1H), 6.73-7.88 (m, 8H). 31P NMR (CDCl3, 162 MHz): −17.18, 146.67. 13C NMR (CDCl3, 100 MHz): δ22.5, 22.7, 22.8, 23.0, 26.1, 26.3, 26.5, 26.8 (d, J=9 Hz), 27.5 (d, J=10 Hz), 27.7 (d, J=9 Hz), 29.3 (d, J=8 Hz), 30.1 (d, J=16 Hz), 30.3 (d, J=10 Hz), 30.7, 34.7 (d, J=9 Hz), 35.9 (d, J=10 Hz), 48.3, 119.1, 122.5, 128.2, 131.7, 132.9, 134.0, 134.6, 136.7, 137.1, 145.6, 148.1, 150.3.

Example 4

Preparation of Compound (R,R)-ID with the Following Structure ($R_1$, $R_2$ and $R_3$ are H, $R_4$ is Cyclohexyl, and X is Phenyl in its General Structural Formula)

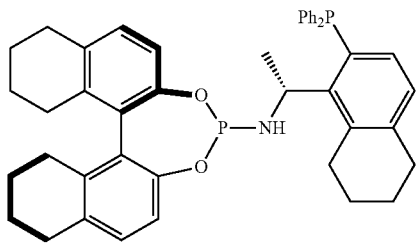

1) To a 200 ml three-neck flask were added 3.2 g (R)-1-cyclohexyl phenylethylamine and 20 ml ethyl ether, and was slowly added 11.96 ml of a hexane solution of n-BuLi with a concentration of 3.2 mol/l at room temperature. After addition, the reaction was continuously stirred at 0° C. for 15 min and then 2.66 ml trimethylchlorosilane was added. 35.8 ml of a hexane solution of n-BuLi with a concentration of 1.6 mol/l was slowly added after 1 h of reaction time and the resulting reaction mixture was slowly warmed up to room temperature within 5 h. After 1 h of reaction time, the resulting reaction mixture was cooled to −20° C. and a solution of 3.44 ml diphenyl phosphine chloride and 20 ml ethyl ether was slowly added. The reaction was warmed up to room temperature and stirred overnight. 40 ml saturated aqueous $NaHCO_3$ was added and then the reaction was continuously stirred for 10 min. The liquid was separated, the aqueous layer was extracted twice with 80 ml ethyl ether, and ether layers were combined, washed with 100 ml water and dried with anhydrous $Na_2SO_4$. The resulting mixture was filtered, the solvent is removed with vacuum, the residue was subjected to column chromatography to obtain a viscous liquid which was recrystallized with n-hexane to give a white crystal, i.e. a phosphine-amine compound (R)-IV (yield: 55%). $^1$HNMR (400 MHz, $CDCl_3$): δ1.48 (d, J=8.8 Hz, 3H); 2.31 (s, 3H); 5.27 (m, 1H), 6.92-7.86 (m, 20H); $^{31}$P NMR ($CDCl_3$): δ-15.84, 51.98; $^{13}$C NMR δ22.5; 34.7; 59.8; 126.2; 127.8; 128.5; 128.6; 128.7; 128.8; 128.9; 129.1; 131.2; 132.1; 132.3; 133.6; 133.8; 133.9; 134.2; 141.7; 142.0; 147.6.

2) To a 200 ml three-neck flask were added 8.5 g of chiral phosphine-containing hydrogenated chloro-$H_8$-BINOL(R)-VII (prepared according to step 4) in Example 1) and 80 ml anhydrous toluene, and a solution of 7.5 g of the chiral phosphine-amine compound (R)-IV prepared in the step 1) and 7.23 g triethylamine in 30 ml toluene was slowly added dropwise at 0° C. After addition, the resulting reaction mixture was warmed up to room temperature and the reaction was continuously stirred overnight. The resulting mixture was filtered and washed with toluene. The residue was dissolved in $CH_2Cl_2$, washed with water and dried with anhydrous $Na_2SO_4$. The solvent was removed to give a white powdery chiral hydrogenated $H_8$-BINOL bisphosphine compound (8.47 g) which was recorded as compound (R,R)-ID. $[\alpha]_D^{24}$=-87 (c 1.02, $CHCl_3$); $^1$H NMR ($CDCl_3$): δ1.33-1.35 (d, J=6.8 Hz, 3H), 3.68-3.75 (m, 1H), 5.37-5.45 (m, 1H), 6.71-7.92 (m, 26H); $^{31}$P NMR ($CDCl_3$): δ-18.0, 152.7; $^{13}$C NMR δ25.6, 48.4, 122.5, 124.7, 125.9, 126.0, 126.9, 127.0, 128.2, 128.3, 128.5, 128.6, 128.7, 129.6, 133.6, 133.8, 133.9, 134.0, 134.1, 136.8, 147.4, 149.4, 150.8.

Example 5

Preparation of Compound (R,R)-IE with the Following Structure ($R_2$, $R_3$ and $R_4$ are H, $R_1$ is Methyl, and X is Phenyl in its General Structural Formula)

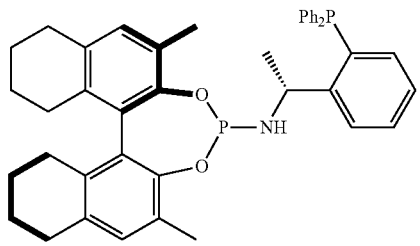

1) To a 200 ml three-neck flask were added 22 g methyl BINOL ((R)-V), 100 ml solvent ethanol and 0.2 g rhodium on carbon, hydrogen at 10 atm was introduced for hydrogenation, then the catalyst was filtered, and ethanol was evaporated to give 22 g chiral hydrogenated (R)$H_8$-BINOL ((R)-VI).

2) 19 g of chiral hydrogenated methyl $H_8$-BINOL ((R)-VI) obtained in step 1), 150 g $PCl_3$ and a catalytic amount of 2-methylpyrrolidone were reacted under reflux until the solid disappeared (about 10 min). Majority of $PCl_3$ is removed under vacuum and a small amount of residual $PCl_3$ was removed by azeotropy with toluene under reduced pressure. After toluene was removed, the residue was recrystallized with n-hexane to give white chiral phosphine-containing hydrogenated chloro-methyl $H_8$-BINOL ((R)-VII: 24 g).

3) To a 200 ml three-neck flask were added 7.65 g of chiral phosphine-containing hydrogenated chloro-methyl $H_8$-BINOL ((R)-VII) and 60 ml anhydrous toluene, and a solution of 7.35 g of the chiral phosphine-amine compound (R)-IV (prepared according to step 4) in Example 1) and 6.12 g triethylamine in 20 ml toluene was slowly added dropwise at 0° C. After addition, the resulting reaction mixture was warmed up to room temperature and the reaction was continuously stirred overnight. The resulting mixture was filtered and washed with toluene. The residue was dissolved in $CH_2Cl_2$, washed with water and dried with anhydrous $Na_2SO_4$. The solvent was removed to give a white powdery hydrogenated methyl $H_8$-BINOL bisphosphine compound (10.6 g) which was recorded as compound (R,R)-IE. $^1$HNMR (400 MHz, $CDCl_3$): δ1.33-1.35 (m, 3H), 2.43-2.45 (m, 6H), 3.66-3.68 (m, 1H), 5.31-5.35 (m, 1H), 6.92-7.83 (m, 24H); $^{31}$P NMR ($CDCl_3$): δ-16.8, 151.6; $^{13}$C NMR δ17.4, 22.5, 22.7, 27.6, 29.1, 30.3, 56.9, 118.4, 118.8, 126.7, 128.7, 128.9, 128.5, 129.0, 132.6, 133.8, 133.5, 134.0, 134.2, 148.6, 150.1.

Example 6

Preparation of (S)—N-(2'-methyl-6'-Ethyl-Phenyl)-N-(1-Methoxylmethyl)Ethylamine 10.4 mg of (R,R)-IA compound prepared in Example 1 as a ligand and 24 mg tetrabutyl ammonium iodide were successively added to 10 ml of a dichloroethane (degassed) solution containing 5.28 mg [Ir(COD)Cl]$_2$ and stirred for 15 min. In addition, 410 g (2 mol) N-(2'-methyl-6'-ethyl-phenyl)-N-(1-methoxylmethyl)ethylimine was dissolved in 700 ml dichloroethane (degassed). The resulting imine solution and the catalyst solution were successively transferred to an autoclave under inert gas protection, and then replaced with hydrogen at normal pressure and 10 bar for three times respectively. Subsequently, a hydrogen pressure of 80 bar was applied and the autoclave was heated to 50° C. After 18 h of reaction time, the reaction was stopped and the resulting reaction solution was cooled to room temperature. The hydrogen pressure was relieved, and the reaction solution was discharged from the autoclave under pressure. The conversion rate was 100%. Dichloroethane was then removed in a rotary evaporator. The resulting reaction solution was distilled under high vacuum (0.1 mbar) to give 401 g (S)—N-(2'-methyl-6'-ethyl-phenyl)-N-(1-methoxylmethyl)ethylamine (yield: 97%). The optical yield was 93.5% (S).

Example 7

Preparation of (S)—N-(2'-Methyl-6'-Ethyl-Phenyl)-N-(1-Methoxylmethyl)Ethylamine 11.2 mg of compound (R,R)-IB prepared in Example 2 as a ligand and 24 mg tetrabutyl ammonium iodide were successively added to 10 ml of a dichloroethane (degassed) solution containing 5.28 mg [Ir(COD)Cl]$_2$ and stirred for 15 min. In addition, 410 g (2 mol) N-(2'-methyl-6'-ethyl-phenyl)-N-(1-methoxylmethyl)ethylimine was dissolved in 700 ml dichloroethane (degassed). The resulting imine solution and the catalyst solution were successively transferred to an autoclave under inert gas protection, and then replaced with hydrogen at normal pressure and 10 bar for three times respectively. Subsequently, a hydrogen pressure of 80 bar was applied and the autoclave was heated to 50° C. After 18 h of reaction time, the reaction was stopped and the resulting reaction solution was cooled to room temperature. The hydrogen pressure was relieved, and the reaction solution was discharged from the autoclave under pressure. The conversion rate was 100%. Dichloroethane was then removed in a rotary evaporator. The resulting reaction solution was distilled under high vacuum (0.1 mbar) to give 403 g (S)—N-(2'-methyl-6'-ethyl-phenyl)-N-(1-methoxylmethyl)ethylamine (yield: 98%). The optical yield was 92% (S).

Example 8

Preparation of (S)—N-(2'-Methyl-6'-Ethyl-Phenyl-1'-yl)-1-(Methoxylmethyl)Ethylamine 12.1 mg of compound (R,R)-IC prepared in Example 3 as a ligand and 26 mg tetrabutyl ammonium iodide were successively added to 10 ml of a dichloroethane (degassed) solution containing 5.58 mg [Ir(COD)Cl]$_2$ and stirred for 15 min. In addition, 410 g (2 mol) N-(2'-methyl-6'-ethyl-phenyl)-N-(1-methoxylmethyl)ethylimine was dissolved in 700 ml dichloroethane (degassed). The resulting imine solution and the catalyst solution were successively transferred to an autoclave under inert gas protection, and then replaced with hydrogen at normal pressure and 10 bar for three times respectively. Subsequently, a hydrogen pressure of 80 bar was applied and the autoclave was heated to 50° C. After 18 h of reaction time, the reaction was stopped and the resulting reaction solution was cooled to room temperature. The hydrogen pressure was relieved, and the reaction solution was discharged from the autoclave under pressure. The conversion rate was 100%. Dichloroethane was then removed in a rotary evaporator. The resulting reaction solution was distilled under high vacuum (0.1 mbar) to give 400 g (S)—N-(2'-methyl-6'-ethyl-phenyl)-N-(1-methoxylmethyl)ethylamine (yield: 97%). The optical yield was 91% (S).

Example 9

Preparation of (S)—N-(2'-Methyl-6'-Ethyl-Phenyl-1'-yl)-1-(Methoxylmethyl)Ethylamine 12.8 mg of compound (R,R)-ID prepared in Example 4 as a ligand and 28 mg iodobenzene were successively added to 10 ml of a dichloroethane (degassed) solution containing 6.56 mg [Ir(COD)Cl]$_2$ and stirred for 15 min. In addition, 410 g (2 mol) N-(2'-methyl-6'-ethyl-phenyl)-N-(1-methoxylmethyl)ethylimine was dissolved in 700 ml dichloroethane (degassed). The resulting imine solution and the catalyst solution were successively transferred to an autoclave under inert gas protection, and then replaced with hydrogen at normal pressure and 10 bar for three times respectively. Subsequently, a hydrogen pressure of 80 bar was applied and the autoclave was heated to 50° C. After 18 h of reaction time, the reaction was stopped and the resulting reaction solution was cooled to room temperature. The hydrogen pressure was relieved, and the reaction solution was discharged from the autoclave under pressure. The conversion rate was 100%. Dichloroethane was then removed in a rotary evaporator. The resulting reaction solution was distilled under high vacuum (0.1 mbar) to give 406 g (S)—N-(2'-methyl-6'-ethyl-phenyl)-N-(1-methoxylmethyl)ethylamine (yield: 98%). The optical yield was 90% (S).

Example 10

Preparation of (S)—N-(2'-Methyl-6'-Ethyl-Phenyl-1'-yl)-1-(Methoxylmethyl)Ethylamine 13.2 mg of compound (R,R)-IE prepared in Example 5 as a ligand and 28 mg iodobenzene were successively added to 10 ml of a dichloroethane (degassed) solution containing 6.56 mg [Ir(COD)Cl]$_2$ and stirred for 15 min. In addition, 410 g (2 mol) N-(2'-methyl-6'-ethyl-phenyl)-N-(1-methoxylmethyl)ethylimine was dissolved in 700 ml dichloroethane (degassed). The resulting imine solution and the catalyst solution were successively transferred to an autoclave under inert gas protection, and then replaced with hydrogen at normal pressure and 10 bar for three times respectively. Subsequently, a hydrogen pressure of 80 bar was applied and the autoclave was heated to 50° C. After 18 h of reaction time, the reaction was stopped and the resulting reaction solution was cooled to room temperature. The hydrogen pressure was relieved, and the reaction solution was discharged from the autoclave under pressure. The conversion rate was 100%. Dichloroethane was then removed in a rotary evaporator. The resulting reaction solution was distilled under high vacuum (0.1 mbar) to give 406 g (S)—N-(2'-methyl-6'-ethyl-phenyl)-N-(1-methoxylmethyl)ethylamine (yield: 98%). The optical yield was 93% (S).

Example 11

Preparation of (S)—N-(2'-Methyl-6'-Ethyl-Phenyl-1'-yl)-1-(Methoxylmethyl)Ethylamine The method was the same as that of Example 6 except that 40 g acetic acid was added to the reaction system. 406 g (S)—N-(2'-methyl-6'-ethyl-phenyl)-N-(1-methoxylmethyl)ethylamine (yield: 98%) was finally obtained. The optical yield was 92.5% (S).

Example 12

Preparation of (S)-2-Chloro-N-(2'-Ethyl-6'-Methylphenyl)-N-(2-Methoxyl-1-Methylethyl)Acetamide Under stirring and nitrogen protection, 538 g (5.79 mol) pyridine was added to a mixed solution of 1000 g (4.83 mol) (S)—N-(2'-ethyl-6'-methylphenyl)-N-(1-methoxylmethyl)ethylamine (active component: 93%) and 1800 ml toluene at 15-20° C. over 30 min. Subsequently, the resulting solution was cooled to below 15-20° C. in ice-salt bath and 656 g (5.81 mol) chloroacetyl chloride was added dropwise over 1.5 h. After dropwise addition, the resulting suspension was stirred at room temperature for 1.5 h. The reaction mixture was poured into 2000 ml water and extracted twice with 200 ml toluene each time. Organic phases were combined, washed once with 400 ml 1N hydrochloric acid, washed twice with 400 ml of a saturated sodium chloride solution, washed once with 500 ml of a saturated sodium bicarbonate solution, and dried with sodium sulfate and filtered, and the solvent was removed under vacuum. A crude product of (S)-2-chloro-N-(2'-ethyl-6'-methylphenyl)-N-(2-methoxyl-1-methylethyl)acetamide ((S)-metolachlor) was obtained, wherein the content of the active component was 92% and the yield was 96%.

What is claimed is:

1. A chiral hydrogenated $H_8$-BINOL bisphosphine compound with the structure shown as the following formula (I):

(I)

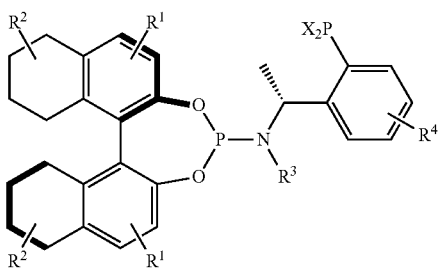

wherein both $R^1$ and $R^2$ are halogen, H or $C_1$-$C_{10}$ aliphatic group; $R^3$ is H or $C_1$-$C_{10}$ aliphatic group; $R^4$ is halogen, amino, nitro, H, $C_1$-$C_{10}$ aliphatic group or $C_1$-$C_{10}$ aromatic group; and X is

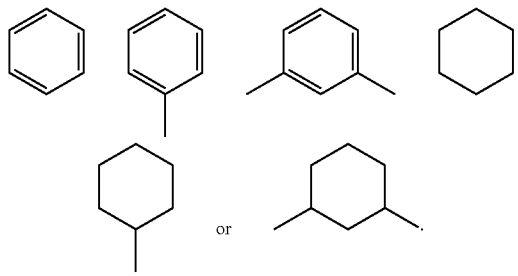

2. A catalyst for an asymmetric catalytic hydrogenation reaction comprising an iridium-containing coordination compound formed by combining (a) a chiral hydrogenated $H_8$-BINOL bisphosphine compound as a ligand and (b) an iridium-cyclooctadiene complex, wherein the chiral hydrogenated $H_8$-BINOL bisphosphine has the following formula (I):

(I)

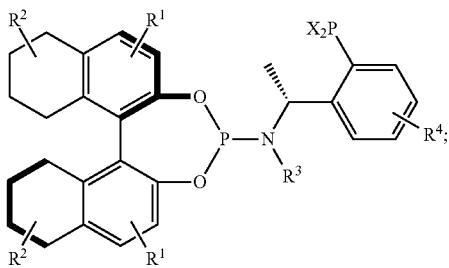

and wherein both $R^1$ and $R^2$ are halogen, H or $C_1$-$C_{10}$ aliphatic group; $R^3$ is H or $C_1$-$C_{10}$ aliphatic group; $R^4$ is halogen, amino, nitro, H, $C_1$-$C_{10}$ aliphatic group or $C_1$-$C_{10}$ aromatic group; and X is

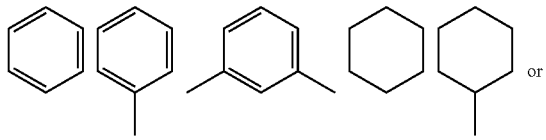

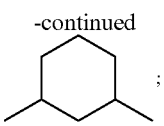

and wherein a molar ratio of (a) to (b) is 0.5-5:1.

3. The catalyst as claimed in claim 2, wherein the iridium-cyclooctadiene complex is any one of $[IrCl(COD)]_2$, $[IrBr(COD)]_2$ or $[Ir(COD)_2]BF_4$.

4. The catalyst as claimed in claim 2 further comprising a halogen-containing additive, wherein a molar ratio of the halogen-containing additive to the iridium-containing coordination compound catalyst is 0.001-10:1.

5. The catalyst as claimed in claim 4, wherein the halogen-containing additive is selected from an alkali metal salt of a halogen family element, a halogen-containing $C_1$-$C_{60}$ quaternary ammonium salt, or a halogen-containing $C_1$-$C_{60}$ aromatic hydrocarbon or aliphatic hydrocarbon.

6. The catalyst as claimed in claim 5, wherein the halogen is chlorine, bromine or iodine.

7. The catalyst as claimed in claim 5, wherein the halogen-containing additive is selected from iodobenzene, tetrabutyl ammonium iodide or other iodine-containing $C_1$-$C_{60}$ quaternary ammonium salt.

8. A method of conducting an asymmetric catalytic hydrogenation reaction, the method comprising the step of:
catalyzing the asymmetric hydrogenation of a compound selected from the group consisting of N-alkyl imine, N-arylimine, N-aromatic heterocyclic imine, N acyl hydrazone, N-acyl sulfimide, N-acyl phosphinoimide, an aromatic azacyclic ring, and a non-aromatic azacyclic ring with the catalyst according to claim 2.

9. The method as claimed in claim 8, wherein the asymmetric hydrogenation reaction is carried out at a temperature of −20 to 150° C.

10. The method as claimed in claim 8, wherein the asymmetric hydrogenation reaction is carried out at a pressure of 5-150 atm.

11. The method as claimed in claim 8, wherein a molar ratio of a reaction substrate and the catalyst is 500-5,000,000:1 in the asymmetric hydrogenation reaction.

12. The method as claimed in claim 8, wherein an organic or inorganic acid additive is added in an amount of 0.001-60% based on the weight of a reaction substrate in the asymmetric hydrogenation reaction.

13. The method as claimed in claim 12, wherein the organic or inorganic acid additive is selected from the group consisting of acetic acid, chloroacetic acid, propionic acid, trifluoroacetic acid, sulfuric acid, phosphoric acid or methanesulfonic acid, and a mixture of more than two thereof.

14. The method as claimed in claim 8, wherein the compound is selected from the group consisting of

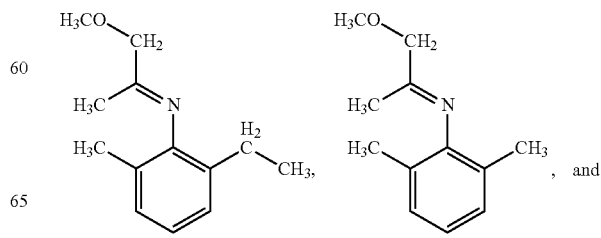

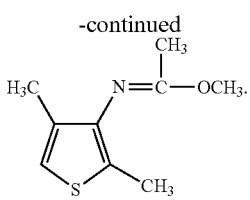

15. A method of preparing a chiral herbicide (S)-metolachlor, the method comprising the steps of:

reacting N-(2'-methyl-6'-ethylphenyl)-N-(1-methoxylmethyl)ethylimine in the presence of the catalyst according to claim 2 to obtain a chiral hydrogenated product (S)—N-(2'-methyl-6'-ethylphenyl)-N-(1-methoxylmethyl)ethylamine, and then using the chiral hydrogenated product as a precursor to synthesize the chiral herbicide (S)-metolachlor.

16. A method for preparing a chiral hydrogenated H$_8$-BINOL bisphosphine compound having the following formula (I):

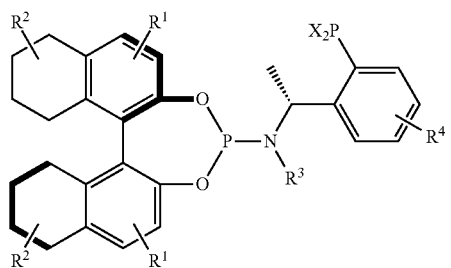

(I)

wherein both R$^1$ and R$^2$ are halogen, H or C$_1$-C$_{10}$ aliphatic group; R$^3$ is H or C$_1$-C$_{10}$ aliphatic group; R$^4$ is halogen, amino, nitro, H, C$_1$-C$_{10}$ aliphatic group or C$_1$-C$_{10}$ aromatic group; and X is

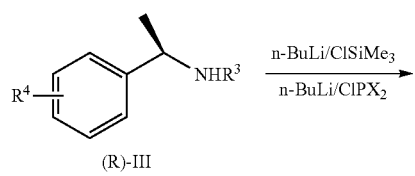

, the method comprising the steps of:

(1) converting (R)-III to (R)-IV as follows in sub-steps (1a) through (1h)

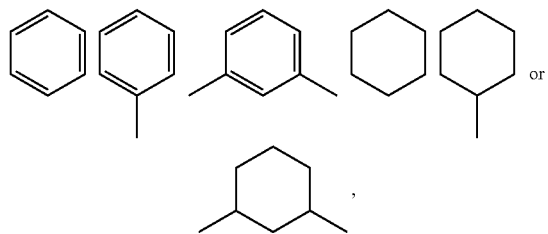

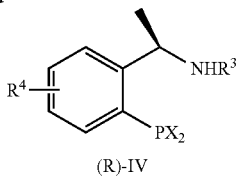

(1a) based on molar ratio of phenylethylamine (R)-III: n-BuLi:ClSiMe$_3$:n-BuLi:ClPX$_2$=1:1-3:1-3:3-6:1-5, dissolving phenylethylamine (R)-(III) in ethyl ether;

(1b) adding n-BuLi and then ClSiMe$_3$ after continuous stirring of the reaction mixture at 0° C.;

(1c) adding n-BuLi to the reaction mixture after 0.5-10 h of reaction of the reaction mixture after step (1b);

(1d) carrying out the reaction for 2-10 h to obtain a resulting reaction mixture;

(1e) adding the resulting reaction mixture to a solution of ClPX$_2$ with cooling;

(1f) allowing the reaction mixture to stand overnight at 0-50° C.;

(1g) adding 2M HCl to quench the reaction; and (1h) performing column chromatography to obtain a phosphine-amine compound (R)-IV;

(2) converting (R)-V to (R)-VI as follows in sub-steps (2a) through (2g)

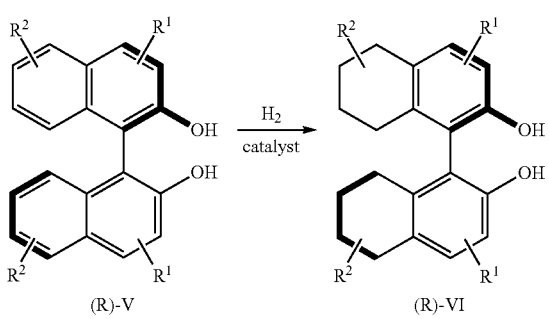

(2a) based on weight ratio of BINOL(V): rhodium/platinum on carbon catalyst:ethanol=1:0.01-0.2:1-10, adding BINOL(V), rhodium/platinum on carbon catalyst, and ethanol to an autoclave;

(2b) flushing with hydrogen several times;

(2c) warming up to 10-100° C.;

(2d) increasing hydrogen pressure to 5-40 atm;

(2e) after hydrogen is no longer absorbed in the reaction, cooling;

(2f) filtering; and (2g) removing the solvent under vacuum, thereby obtaining hydrogenated H$_8$-BINOL(VI);

(3) converting (R)-VI to (R)-VII as follows in sub-steps (3a) through (3e)

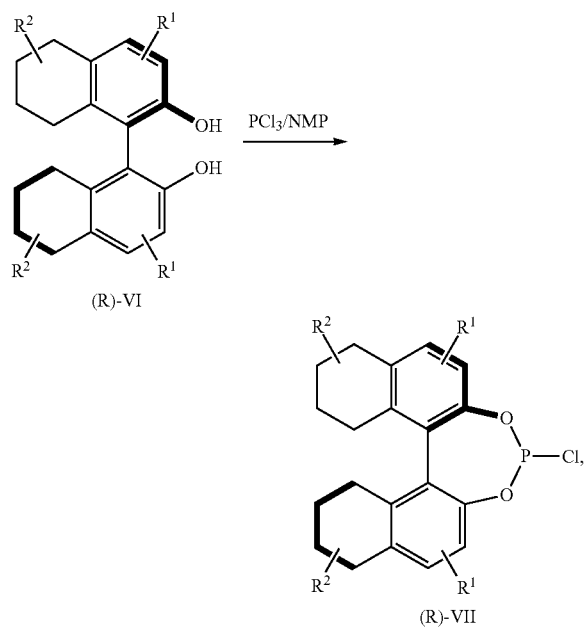

(R)-VI

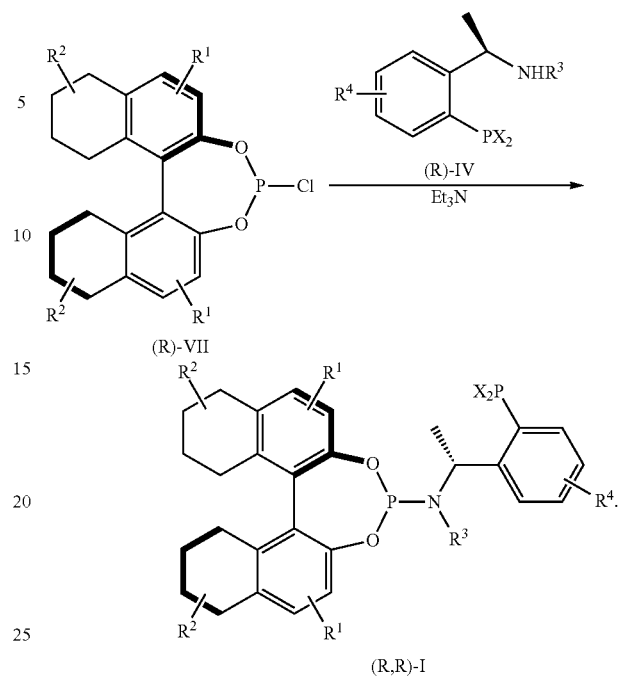

(3a) based on molar ratio of the hydrogenated H₈-BINOL(VI) obtained in step (2): PCl₃:2-methylpyrrolidone=1:5-10:0.001-0.01, charging hydrogenated H₈-BINOL(VI) and PCl₃ into a reaction flask;
(3b) adding 2-methylpyrrolidone;
(3c) heating under reflux to react until hydrogenated H₈-BINOL(VI) is fully dissolved;
(3d) removing the solvent under vacuum leaving a residue; and
(3e) recrystallizing the residue with n-hexane to obtain the hydrogenated phosphine-containing chloro-H₈-BINOL(VII); and
(4) converting (R)-VII to (R,R)-I as follows in sub-steps (4a) through (4f)

(4a) based on molar ratio of compound (R)-IV obtained in step (1h): compound (R)-VII obtained in step (3e): Et₃N (triethylamine)=1:1-2:3-5, dissolving compound (R)-VII in toluene;
(4b) adding a solution of compound (R)-IV and NEt₃ in toluene at 0-50° C.;
(4c) warming the reaction mixture to 0-95° C.;
(4d) reacting for 1-30 h with stirring;
(4e) filtering; and
(4f) removing the solvent, thereby obtaining the chiral hydrogenated H₈-BINOL bisphosphine compound (R,R)-I.

\* \* \* \* \*